US011393110B2

(12) United States Patent
Holladay et al.

(10) Patent No.: US 11,393,110 B2
(45) Date of Patent: Jul. 19, 2022

(54) SPATIAL REGISTRATION OF TRACKING SYSTEM WITH AN IMAGE USING TWO-DIMENSIONAL IMAGE PROJECTIONS

(71) Applicant: CENTERLINE BIOMEDICAL, INC., Cleveland, OH (US)

(72) Inventors: Matthew Holladay, Cleveland, OH (US); Vikash Goel, Cleveland, OH (US)

(73) Assignee: CENTERLINE BIOMEDICAL, INC., Cleveland, OH (US)

( * ) Notice: Subject to any disclaimer, the term of this patent is extended or adjusted under 35 U.S.C. 154(b) by 210 days.

(21) Appl. No.: 16/840,862

(22) Filed: Apr. 6, 2020

(65) Prior Publication Data
US 2020/0320721 A1 Oct. 8, 2020

Related U.S. Application Data

(60) Provisional application No. 62/829,394, filed on Apr. 4, 2019.

(51) Int. Cl.
*G06T 7/33* (2017.01)
*G06T 3/00* (2006.01)
(Continued)

(52) U.S. Cl.
CPC .......... *G06T 7/337* (2017.01); *A61B 6/4441* (2013.01); *A61B 6/481* (2013.01); *A61M 5/007* (2013.01);
(Continued)

(58) Field of Classification Search
None
See application file for complete search history.

(56) References Cited

U.S. PATENT DOCUMENTS 6,533,455 B2 3/2003 Mann et al.
7,010,095 B2 3/2006 Mitschke et al.
(Continued)

FOREIGN PATENT DOCUMENTS

EP 1421913 A1 5/2004
JP 2005021675 A 1/2005
(Continued)

OTHER PUBLICATIONS

Applicant: Centerline Biomedical, Inc.; PCT International Search Report and PCT Written Opinion; International Application No. PCT/US2020/026865; Filing Date: Apr. 6, 2020; Authorized Officer Kang Min Jeong; dated Jul. 23, 2020; 12 pgs.
(Continued)

*Primary Examiner* — James A Thompson
(74) *Attorney, Agent, or Firm* — Tarolli, Sundheim, Covell & Tummino LLP

(57) ABSTRACT

An example method includes acquiring a first image using a medical imaging modality that includes a two-dimensional field of view to include a patient and a multi-modal marker. A second image is acquired using the medical image modality. The second image includes the patient and the multi-modal marker and is along a non-coincident angle with respect to the first image. Predetermined portions of the multi-modal marker are visible in the first and second images and have a known location and orientation with respect to at least one sensor detectable by a tracking system. The method also includes estimating a three-dimensional position for predetermined portions of the multi-modal marker. The method also includes determining an affine transformation for registering a three-dimensional coordinate system of the tracking system with a three-dimensional coordinate system of the medical imaging modality.

23 Claims, 7 Drawing Sheets

(51) Int. Cl.
*G06T 17/20* (2006.01)
*G06T 7/246* (2017.01)
*A61M 5/00* (2006.01)
*A61B 6/00* (2006.01)
*G06T 7/73* (2017.01)
*A61B 90/00* (2016.01)

(52) U.S. Cl.
CPC ............ *G06T 3/0075* (2013.01); *G06T 7/248* (2017.01); *G06T 7/74* (2017.01); *G06T 17/20* (2013.01); *A61B 2090/3925* (2016.02); *A61B 2090/3966* (2016.02); *A61B 2090/3995* (2016.02); *G06T 2207/10064* (2013.01); *G06T 2207/10116* (2013.01); *G06T 2207/30204* (2013.01); *G06T 2210/41* (2013.01)

(56) References Cited

U.S. PATENT DOCUMENTS

| | | | |
|---|---|---|---|
| 7,556,428 | B2 | 7/2009 | Sukovic et al. |
| 7,671,887 | B2 | 3/2010 | Pescatore et al. |
| 7,824,328 | B2 | 11/2010 | Gattani et al. |
| 8,060,185 | B2 | 11/2011 | Hunter et al. |
| 8,213,693 | B1 | 7/2012 | Li |
| 8,224,632 | B2 | 7/2012 | Whirley et al. |
| 8,238,625 | B2 | 8/2012 | Strommer et al. |
| 8,248,413 | B2 | 8/2012 | Gattani et al. |
| 8,301,226 | B2 | 10/2012 | Csavoy et al. |
| 8,315,355 | B2 | 11/2012 | Mohamed |
| 8,467,853 | B2 | 6/2013 | Hunter et al. |
| 9,240,043 | B2 | 1/2016 | Carrell et al. |
| 10,176,582 | B2 | 1/2019 | Carrell et al. |
| 10,650,513 | B2 | 5/2020 | Penney et al. |
| 2002/0131559 | A1 | 9/2002 | Launay et al. |
| 2003/0011624 | A1 | 1/2003 | Ellis |
| 2007/0055128 | A1 | 3/2007 | Glossop |
| 2008/0020362 | A1 | 1/2008 | Cotin et al. |
| 2009/0227861 | A1 | 9/2009 | Ganatra et al. |
| 2010/0210938 | A1 | 8/2010 | Verard |
| 2010/0312094 | A1 | 12/2010 | Guttman et al. |
| 2011/0026793 | A1 | 2/2011 | Goel |
| 2011/0054300 | A1 | 3/2011 | Yamamoto et al. |
| 2011/0166446 | A1 | 7/2011 | Whitmore, III et al. |
| 2011/0295109 | A1 | 12/2011 | Lavallee et al. |
| 2012/0014498 | A1 | 1/2012 | Akahori |
| 2013/0079628 | A1 | 3/2013 | Groszmann |
| 2013/0094745 | A1* | 4/2013 | Sundar .................. G06T 3/0068 382/132 |
| 2014/0276002 | A1* | 9/2014 | West ..................... A61B 5/061 600/424 |
| 2015/0138186 | A1 | 5/2015 | Carrell et al. |
| 2016/0242724 | A1 | 8/2016 | Surgivisio |
| 2018/0040147 | A1 | 2/2018 | Alhrishy et al. |
| 2018/0144501 | A1 | 5/2018 | Albiol Colomer et al. |
| 2019/0239838 | A1* | 8/2019 | Barak .................... G06T 7/251 |
| 2019/0304108 | A1 | 10/2019 | Carrell et al. |
| 2020/0260964 | A1* | 8/2020 | Collins .................. A61B 5/743 |
| 2020/0275901 | A1* | 9/2020 | Takemoto ......... A61M 25/0108 |
| 2020/0405397 | A1* | 12/2020 | Liu ........................ A61B 90/39 |

FOREIGN PATENT DOCUMENTS

| | | |
|---|---|---|
| JP | 2007185278 A | 7/2007 |
| JP | 2007209531 A | 8/2007 |
| JP | 2008061858 A | 3/2008 |
| JP | 2008136850 A | 6/2008 |
| JP | 2009072317 A | 4/2009 |
| JP | 2012147858 A | 8/2012 |
| JP | 2012529352 A | 11/2012 |
| WO | 2005119578 A2 | 12/2005 |
| WO | 2008/035271 A2 | 3/2008 |
| WO | 2010/074986 A1 | 7/2010 |
| WO | 2010086374 A1 | 8/2010 |
| WO | 2012127353 A1 | 9/2012 |
| WO | 2012143290 A1 | 10/2012 |

OTHER PUBLICATIONS

Mohapatra, et al., "Radiation Exposure to Operating Room Personnel and Patients During Endovascular Procedures", Journal of Vascular Surgery, 2013, pp. 1-8.

\* cited by examiner

SPATIAL REGISTRATION OF TRACKING SYSTEM WITH AN IMAGE USING TWO-DIMENSIONAL IMAGE PROJECTIONS

CROSS-REFERENCE TO RELATED APPLICATION

This application claims priority from U.S. provisional application No. 62/829,394, filed Apr. 4, 2019, and entitled SPATIAL REGISTRATION OF TRACKING SYSTEM WITH AN IMAGE USING TWO-DIMENSIONAL IMAGE PROJECTIONS, which is incorporated herein by reference in its entirety.

TECHNICAL FIELD

This disclosure relates generally to systems and methods for registering a tracking system with an image space using two-dimensional image projections.

BACKGROUND

Image registration is the process of determining a spatial transformation to bring two or more image coordinate systems into alignment with one another. One example is registration of computed tomography (CT) and cone beam computed tomography (CBCT) images. For instance, the CT image may be obtained in advance of a procedure, such as days or weeks prior to a procedure (e.g., study or treatment). The CBCT image may be obtained just before or at the time of the procedure. The CBCT image set is mathematically processed to spatially register it with the prior CT image. This sort of CT and CBCT registration is used for a variety of purposes, such as planning, diagnosis and treatment (e.g., interventional radiology, image guided therapy and the like). However, equipment to acquire CBCT images may not be available. Additionally, CBCT imaging typically involves a significant of radiation energy for patients and health care personnel.

SUMMARY

This disclosure relates generally to systems and methods for registering a tracking system with an image space using one or more two-dimensional image projections.

As an example, a method includes acquiring a first two-dimensional projection image using a medical imaging modality. The first image includes a two-dimensional field of view that includes a patient and a multi-modal marker. The method also includes acquiring a second two-dimensional projection image using the medical image modality. The second image includes the patient and the multimodal marker and is along a non-coincident angle with respect to the first projection image. Predetermined portions of the multi-modal marker are visible in the first projection image and the second projection image and have a known location and orientation with respect to at least one sensor detectable by a tracking system. The method also includes estimating a three-dimensional position for predetermined portions of the multi-modal marker with respect to a coordinate system of the medical imaging modality according to locations of the predetermined portions in each of the respective first and second two-dimensional projection images. The method also includes determining an affine transformation for registering a three-dimensional coordinate system of the tracking system with a three-dimensional coordinate system of the medical imaging modality based on the estimated position for the respective predetermined portions of the multi-modal marker and a known relationship of the at least one sensor and the predetermined portions of the multi-modal marker.

As another example, a system includes one or more non-transitory computer-readable media to store data and instructions executable by a processor. The data includes prior three-dimensional image data acquired for a patient. The data also includes two-dimensional image data that includes at least one two-dimensional image acquired by a medical imaging modality to include the patient and a multi-modal marker. Predetermined portions of the multi-modal marker are visible in the at least one two-dimensional image and have a known location and orientation with respect to at least one tracking sensor detectable by a tracking system. The instructions are programmed to perform a method comprising:

estimating a three-dimensional position for predetermined portions of the multi-modal marker with respect to a coordinate system of the medical imaging modality according to respective locations of the predetermined portions in each of the at least one two-dimensional image; and determining an affine transformation for registering a three-dimensional coordinate system of the tracking system with a three-dimensional coordinate system of the medical imaging modality based on the estimated position for the respective predetermined portions of the multi-modal marker and a known relationship of the at least one tracking sensor and the predetermined portions of the multi-modal marker.

As a further example, a method includes acquiring a first two-dimensional projection image using a medical imaging modality, the first image including a two-dimensional field of view that includes a patient and a multi-modal marker. The method also includes acquiring a second two-dimensional projection image using the medical image modality, the second image including the patient and the multimodal marker and being along a non-coincident angle with respect to the first projection image. Predetermined portions of the multi-modal marker being visible in the first projection image and the second projection image and having a known location and orientation with respect to at least one sensor detectable by a tracking system. The method also includes deriving respective forward projections from the prior three-dimensional image that correspond to each of the first two-dimensional projection image and the second two-dimensional projection image. The method also includes determining an affine transformation from the coordinate system of the medical imaging modality to the coordinate system of the prior three-dimensional image based on registering the first and second projection images with the respective forward projections.

As yet another example, a system may include one or more non-transitory computer-readable media to store data and instructions executable by a processor. The data includes: prior three-dimensional image data acquired for a patient. The data also includes two-dimensional image data that includes at least one two-dimensional image acquired by a medical imaging modality to include the patient and a multi-modal marker. Predetermined portions of the multi-modal marker are visible in the at least one two-dimensional image and have a known location and orientation with respect to at least one tracking sensor detectable by a tracking system. The instructions are programmed to perform a method comprising:

deriving respective forward projections from the prior three-dimensional image that correspond to each of the two-dimensional images; and determining an affine transformation between the coordinate system of the medical imaging modality and the coordinate system of the prior three-dimensional image based on registering each of the two-dimensional images with the respective forward projections.

DETAILED DESCRIPTION

Figure 1:
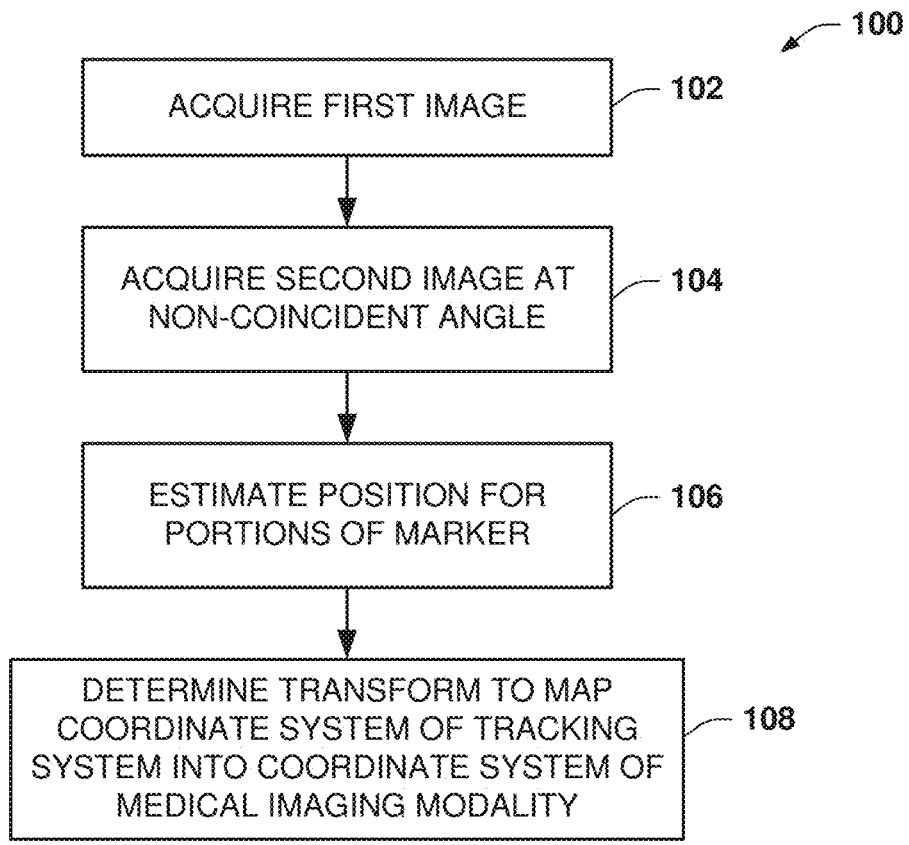
FIG. 1 is a flow diagram depicting an example of a method to register sensors of a tracking system into a spatial coordinate system of a medical imaging modality.

This disclosure relates generally to methods and systems for registering a tracking system with an interventional image space. The approaches disclosed herein can be implemented using reduced ionizing radiation compared to many existing approaches.

The method utilizes a marker device (e.g., a multi-modal marker) that includes fiducial markers detectable by more than one modality. For example, the marker device may include a first fiducial marker to provide a pattern that is visible in an image generated by a medical imaging modality. The medical imaging modality may be fluoroscopy, X-ray or another modality such as ultrasound, configured to provide the image as a two-dimensional projection, which includes a part of a patient and the first fiducial marker. In some examples, the marker device may be configurable to select whether or not the first pattern is visible in subsequent images acquired by the medical imaging modality. The marker device also includes one or more second fiducial markers (e.g., one or more sensors) detectable by a three-dimensional spatial tracking system. The second fiducial markers are arranged in a predetermined spatial position and orientation known with respect to the spatial position of first fiducial marker, which is discernable from the image acquired by the medical imaging modality.

As a further example, the imaging modality can be used to acquire two-dimensional image projections and to store the images in memory (e.g., as DICOM image files). Each of the images includes a field of view that includes the patient and the marker pattern corresponding to the first fiducial marker of the marker device. Thus, during acquisition, the marker is configured (e.g., radiopaque) to enable the marker pattern to be visible in the acquired images. Each of the images is processed to locate and identify predetermined portions of the pattern in each respective image. The identified portions (e.g., points or regions) of the marker pattern are converted to corresponding three-dimensional locations in a three-dimensional spatial coordinate system of the medical imaging modality. An affine transform is computed to map the sensor position to the coordinate system of the medical imaging modality (or to map the marker pattern locations in the imaging modality coordinate system to the coordinate system of the tracking system) based on the spatial relationship between each of the first and second fiducial markers of the marker device. As mentioned, the spatial relationship is already known (and stored in memory) based on the geometry of the pattern of the first fiducial marker and sensors of the second fiducial marker implemented on the tracking device. Thus, the transform enables the systems and methods to register position and orientation information provided by the tracking system into the coordinate system of the medical imaging modality (or the inverse thereof) based on a small number (e.g., two or three) of projection images, which results in greatly reduced ionizing radiation compared to many existing approaches (e.g., cone beam computed tomography).

After such transform is determined, a second affine transform may be determined to map from the spatial coordinate system of the medical imaging modality to another three-dimensional spatial coordinate system, such as corresponding to a pre-operative three-dimensional image scan. For example, the pre-operative three-dimensional image scan may be a high-resolution imaging technique, such as computed tomography or magnetic resonance imaging, which may be performed hours, days or even weeks in advance of a procedure. The second affine transform may be determined by registering the first and second (or more) projection images, which were acquired using the medical imaging modality described above, with corresponding projections (e.g., along the same angles) derived from the pre-operative three-dimensional image scan.

FIG. 1 is a flow diagram depicting an example of a method 100 for registering a coordinate system of a tracking system into a coordinate system of a medical imaging modality (e.g., a fluoroscopy or x-ray system). One or more sensors are integrated into a multi-modal marker device, which includes an arrangement of fiducial markers having a known spatial relationship with respect to each other. The fiducial markers include a set of markers (e.g., sensors) that are detectable by the tracking system and another set of markers (e.g., radiopaque markers) that are visible in images acquired by the imaging modality. The method thus will be described with respect to a tracking system and a medical imaging modality.

As an example, the medical imaging modality is configured to provide image data (e.g., DICOM image file) representing a two-dimensional image projection. For example, the medical imaging modality can be an X-ray system, such as a flat panel X-ray system, a biplane X-ray system, a C-arm fluoroscopy system, an ultrasound imaging system or the like.

As a further example, the marker device includes one or more sensors configured to indicate a three-dimensional position in a coordinate system of the tracking system. For example, the tracking system is an electromagnetic tracking system that generates an electromagnetic field. Each sensor provides a sensor signal based on the electromagnetic field, which is converted into position and orientation information for each respective sensor. An example electromagnetic field tracking system is commercially available from Northern Digital, Inc., of Ontario, Canada. The tracking system can provide the tracking data at an output sample rate (e.g., sixty samples per second) for each sensor sufficient to enable substantially real time determination of sensor location (e.g., to provide a vector describing sensor position and orientation). The tracking system thus can process each frame of tracking data such that the tracking data can likewise represent real time tracking data acquired by the tracking system, which can be registered into a coordinate system of an imaging system, as disclosed herein. In some examples, each sensor can be detectable by the tracking system to enable tracking the sensor in five or six degrees of freedom. Other types of sensors and tracking system may be used in other examples.

At 102, the method 100 includes acquiring a first two-dimensional projection image using the medical imaging modality. The first image thus includes a two-dimensional image projection for a field of view that includes a patient (a region of interest of the patient's body) and a multi-modal marker. As disclosed herein, the multi-modal marker includes a sensor to determine a three-dimensional position in a tracking system coordinate space and a second marker (e.g., fiducial pattern) that is detectable by the medical imaging modality. The sensor and second marker may be co-located or have other fixed relative positions that are known with respect to each other a priori.

At 104, the method includes acquiring a second two-dimensional projection image using the medical image modality. The second image also includes the patient and the multimodal marker though is taken along a non-coincident angle (e.g., less than or equal to about 90 degrees) with respect to angle along which the first image is acquired. There can be any number of total images; although the number is kept low, such as less than ten (e.g., 5 or 2 images) to reduce the exposure to ionizing radiation compared to other modalities, such as CBCT. As an example, the imaging modality can be configured to acquire (at 102 and 104) the images to include a right anterior oblique projection, a left anterior oblique projection as well as other projections (e.g., an anterior-posterior projection). In each of the images, predetermined portions of a radiopaque fiducial marker of the multi-modal marker device are visible. There may be one or more radiopaque fiducial markers on the multi-modal marker device, each having a known location and orientation with respect to one or more respective tracking sensors detectable by a tracking system. As used herein, radio opaque refers to the inability of ionizing electromagnetic radiation to pass through sufficient to make the objects visible in a corresponding image obtained by an imaging modality (e.g., two-dimensional (2D) medical imaging modality 456). Thus, the radio opaque objects can be radio-dense materials with respect to the imaging modality. In an example where two images are acquired (e.g., anterior-posterior and lateral projections), the multi-modal marker device may include three spaced apart radio-opaque markers (e.g., spheres) and the markers are arranged so as to not all be co-linear in each of the images. In another example, a single marker could be used; however, the medical imaging modality would need to acquire at least three images along different relative projection angles.

At 106, a three-dimensional position is estimated for respective predetermined portions of the multi-modal marker with respect to a coordinate system of the medical imaging modality based on the locations of such predetermined portions in each of the respective images. At 106, the locations for each of the predetermined portions of the multimodal marker are also determined in the tracking coordinate system, such as to provide a set of points in tracking system space. Thus, the same portions of one or more markers (e.g., coordinates in the respective spatial domains) are identified in both the intraoperative imaging coordinate system and the tracking system coordinate system. The number of points will vary depending on the construction and number of marker devices that are used.

Figure 7B:
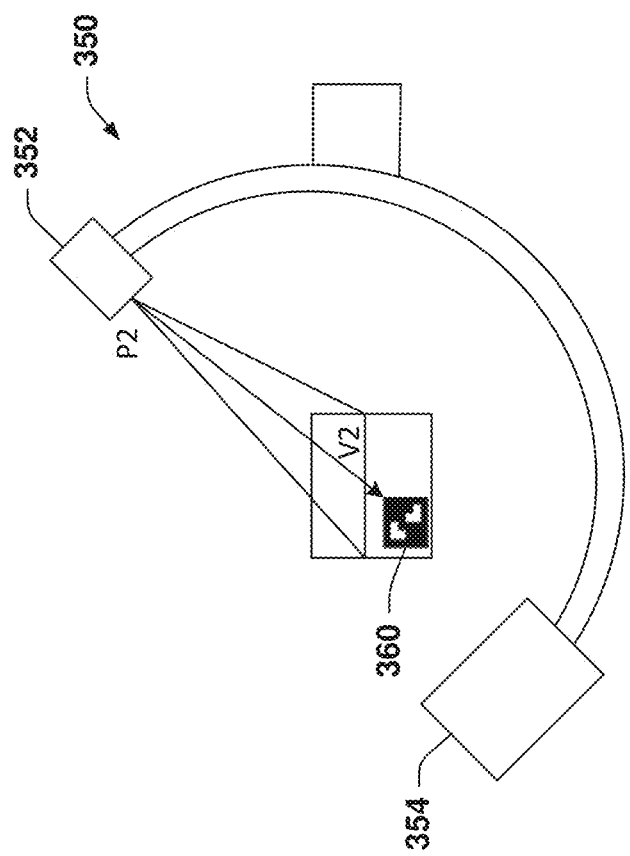
FIGS. 7A and 7B depict a schematic example of a medical imaging modality.
Figure 7A:
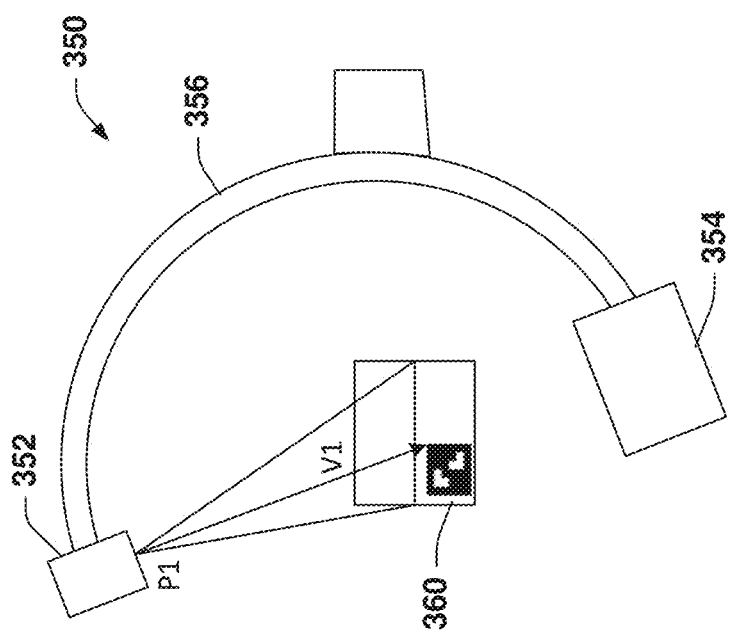

As one example, the fiducial marker(s), which is represented in the images acquired from the imaging modality at 102 and 104, may include a radiopaque material in the form of a rectangular-shaped marker border having respective corners where edges thereof meet. For example, the radiopaque material is provided on the marker device in a form to represent an ArUco marker (see, e.g., Open Source Computer Vision Library: http://opencv.org). In this way, an established image processing algorithm (e.g., detectMarkers( ) function of the OpenCV library) may be implemented to detect and identify respective corners from the image projection (images acquired at 102 and 104) that includes a representation of the ArUco-type fiducial marker. Other related parameters may also be determined by the image processing algorithm. An example of such an ArUco marker is show in FIGS. 3, 4A, 7A and 7B. FIGS. 7A and 7B and the corresponding description demonstrate an example of how respective corners of such marker may be located in three-dimensional coordinates of an intraoperative medical imaging modality to enable registration between an intraoperative spatial coordinate system of the medical imaging modality and a pre-operative spatial coordinate system (of a preoperative image space).

As a second example, which may be an alternative or in addition to the ArUco type marker, the radiopaque material may be in the form of three-dimensional objects on or embedded within the marker device, such as in the form of spheres, cones or the like. Spheres are an example of objects that exhibit the same given shape regardless of the viewing angle for a projection 2D image. In this example, each of the spheres has a known spatial position with respect to the coordinates and orientation of the tracking sensor that is also fixed with respect to the marker device. Thus, points for each of the spheres (or other 3D objects) system may be computed at 106 in the tracking coordinate by multiplying a transform for the sensor that defines a fixed, known offset with respect to each respective sphere. In the example where there are three marker devices, each containing three spheres, the estimation at 106 determines three sets of three points each in the tracking system coordinate system. Similarly, the coordinates location of each sphere is determined for each (at least two) of the 2D images that are acquired (at 102 and 104). For example, the spheres are located for each tracking sensor (e.g., using a ClosestPoint method as disclosed herein), and the spheres location (e.g., the center of each sphere) is stored in memory linked to the respective sensor. This results in the same number of points (for each sphere) as determined in the tracking coordinate system.

At 108, an affine transform is determined to map the coordinate system of the tracking system to the coordinate system of the medical imaging modality (also referred to herein as an intraoperative imaging modality). For example, the transform is determined by applying a co-registration method to align the sets of points provided at 106 for each of the tracking coordinate system and the intraoperative coordinate system. As disclosed herein (see, e.g., transform calculators in FIG. 8), some examples of co-registration methods include an error minimization function (e.g., single value decomposition), a change of basis function as well as other functions that may be used to determine the transform at 108.

In some examples, the medical imaging modality includes a C-arm having a center of rotation, an origin of the coordinate system of the medical imaging modality thus may be defined as the center of rotation of the C-arm. The medical imaging system may be modelled as a pinhole camera having corresponding spatial parameters that are used to define a spatial coordinate system for medical imaging modality (e.g., a C-arm). For example, spatial parameters of a C-arm (e.g., center of rotation, rotation angle of C-arm, radius of C-arm) may be measured manually, provided by a manufacture and/or derived from fields of a DICOM image file. The transform determined at 108 can be based on the estimated position for the predetermined portions of the marker(s) determined at 106 and based on known fixed spatial relationship of the predetermined portions of the marker(s) and the tracking sensor(s) of the marker device. As an example, the fixed relationship of the predetermined portions of the marker(s) and sensors may be determined during manufacturing and printed on the marker. As another example, the relationship may be measured (e.g., manually) and entered into a computer (e.g., via user interface) that is programmed to determine the transform at 108. In other examples, the coordinates for each of the points may be determined automatically as relative coordinates in the image data according to pixel locations (e.g., at the centroid or center) of each marker.

Figure 2:
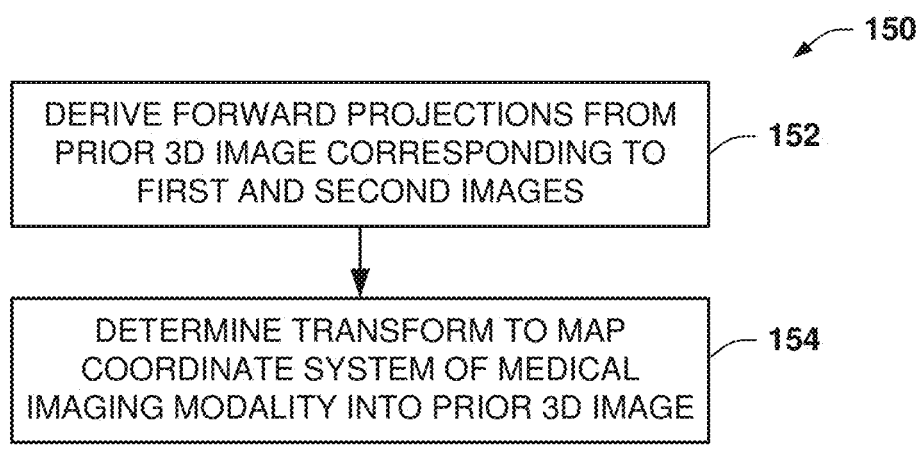
FIG. 2 is a flow diagram for registering from a spatial coordinate system of a medical imaging modality to a spatial coordinate system of a prior three-dimensional image.

FIG. 2 is a flow diagram of a method 150 for registering from a spatial coordinate system of a medical imaging modality to a spatial coordinate system of a prior three-dimensional image, such as is stored in memory (e.g., as DICOM or other image file). For example, the prior three-dimensional image can be acquired by preoperatively for a given patient by a three-dimensional medical imaging modality. As an example, the preoperative image data can correspond to a preoperative arterial CT scan for a region of interest of the patient, such as can be acquired weeks or months prior to a corresponding operation. Other imaging modalities can be used to provide three-dimensional image data, such as MRI, ultrasonography, positron emission tomography or the like. Such scans are common part of preoperative planning in a surgical workflow to help size prostheses and to plan surgery or other interventions.

In some examples, one or more anatomical structures captured in the preoperative image data may be converted to a respective three-dimensional model in the coordinate system of preoperative image. As an example, the model is an implicit model that mathematically describes a tubular anatomic structure (e.g., a patient's vessels), such as including a centerline and surface of the tubular structure. The implicit model may include a small set of parameters such as corresponding to a lofted b-spline (basis spline) function for the elongated anatomical structure. As one example, the anatomical model generator can be programmed to compute the implicit model data according to the disclosure of U.S. Patent Publication No. 2011/0026793 entitled Automated Centerline Extraction Method and Generation of Corresponding Analytical Expression and Use Thereof, which is incorporated herein by reference. Another example of generating an implicit model for tubular anatomical structures is disclosed in *Analytical centerline extraction and surface fitting using CT scans for aortic aneurysm repair*, Goel, Vikash R, Master's Thesis, Cornell University (2005), which is incorporated herein by reference. Other types of geometric representations can also be utilized to provide the implicit model. For example, parameters representing lofted ellipses or triangular meshes can be generated to provide the anatomical model data representing the patient's anatomical structure of interest in three dimensional coordinate system. The three-dimensional mesh that is generated may be stored in memory in addition or as an alternative to the three-dimensional image acquired by the preoperative image modality.

At 152, the method includes deriving respective forward projections from the prior three-dimensional image volume based on the acquired images (e.g., first and second images acquired at 102 and 104). For example, each of the acquired 2D images is registered with corresponding forward 3D projections from the like angles. As an example, two-dimensional LAO and RAO images from a fluoroscopy system are registered by aligning such images (e.g., through translation and rotation) with corresponding LAO and RAO projections derived from a CT image volume. The registration of projection angles may be implemented through manual alignment and/or be automated.

In an example where a three-dimensional mesh has been generated to model an anatomical structure (e.g., vessel) in preoperative three-dimensional image, the mesh may be used to align the with respect to the intraoperative images (e.g., as acquired at 102 and 104). A 3D projection matrix may be applied to the mesh that was generated from the pre-operative image. For example, a "perspective" projection matrix is used if the appropriate parameters for modeling the intraoperative imaging system as a pinhole camera are known. In other examples, a "parallel" project matrix is used. In an example, where the marker device includes radiopaque spheres, the application of the parallel projection matrix should be sufficiently accurate because the spheres on the marker device are close together relative to the focal length of the intraoperative imaging system. If the angle of the C-arm is known for each of the intraoperative images, one 3D projection of the mesh is performed to match the angle for each intraoperative image. If the angle of the C-arm is not known, multiple 3D projections may be generated along different angles and there may be a manual or automated selection of a "best fit" match between the respective 3D projections and the respective two-dimensional image. The end result of this will be pairs of images, in which each image pair includes a 2D intraoperative image and a 2D projection derived from the three-dimensional mesh.

At 154, the method includes determining an affine transformation from the coordinate system of the medical imaging modality to the coordinate system of the prior three-dimensional image based on registering the first and second projection images (e.g., acquired at 102 and 104) with the respective forward projections determined at 152. The transform that is generated at 154 can be stored in memory.

As an example, a co-registration method may be implemented (e.g., as instructions executable by a processor) to determine the transform at 154 for mapping spatial data from the intraoperative 2D image space to the preoperative 3D image space. For example, the transform is determined ay 154 by applying a co-registration method to align sets of points identified for each of the 2D medical images and prior 3D image coordinate systems. In each of the 3D projection images (e.g., derived at 152) and the images that are acquired by the 2D medical imaging modality (at 102 and 104), one or more sets of common points is identified. In an example, the points may be anatomical landmarks or other identifiable fiducial points, such as bony landmarks on the spine, bits of calcification visible in both image set images, or points on vessels such as when contrast is used in both the intraoperative and preoperative images. Because the preoperative image is in three-dimensional space, the user can identify the points using 3 orthogonal views (axial, coronal, and sagittal) to directly measure the x, y, and z locations in the preoperative 3D coordinate system. The points may be identified in each of the images manually or automated methods of feature extraction may be used.

Similar to the determination at 108, examples of co-registration methods that may be used to determine the transform at 154 include an error minimization function (e.g., single value decomposition), a change of basis function as well as other functions. In an example, the same functions may be invoked to generate each of the respective transforms to provide more efficient storage and computations.

By way of example, each of the transforms generated at 108 and 154 may be stored as separate transforms or aggregated together to enable registration of sensors in the tracking system coordinate system to be represented and visualized in the 3D coordinate system of the image volume. In examples where the transforms (determined at 108 and 154) are kept separate, it affords the ability to change one of the transforms without impacting the other. For instance, if the second step (e.g., fluoroscopy to pre-op CT) changes from a manual registration to an automatic registration the approach is still the same and the transform generation method 100 of FIG. 1 does not have to be modified. Additionally, if the transform generation method of FIG. 1 changes, the other transform generation method 150 does not have to be modified. In examples where these transforms are kept separate, an output visualization may be generated by multiplying the two transforms together when rendering an object based on tracking sensor data. The details of the multiplication (e.g., order and whether you multiply by the transform or the inverse transform) depends on whether the view is being rendered in tracking system space, in the imaging modality space, or in coordinate space of the prior three-dimensional (e.g., CT) image space.

As a further example when rendering an output visualization in pre-operative CT space, models for the bones and vasculature (e.g., generated in the pre-op CT image space) may be rendered with no transform and anything tracked in EM space (catheters, guidewires, etc.) would have both transformations applied. In an example, when rendering in tracking system space, the models for the bones and vasculature (being in the pre-op CT image space) would have the inverse of both transforms applied and anything tracked in tracking system space (e.g., objects having one or more tracking sensors, such as catheters, guidewires, etc.) would have no transform applied. Additionally, in an example when rendering in the imaging modality space (e.g., fluoroscopy or the like), the models for the bones and vasculature would have the inverse of the imaging modality to pre-op CT transform (e.g., determined at 154) applied and anything tracked in EM space by tracking sensors (e.g., catheters, guidewires, etc.) would have the tracking system to imaging modality transform (e.g., transform determined at 108) applied.

Figure 3:
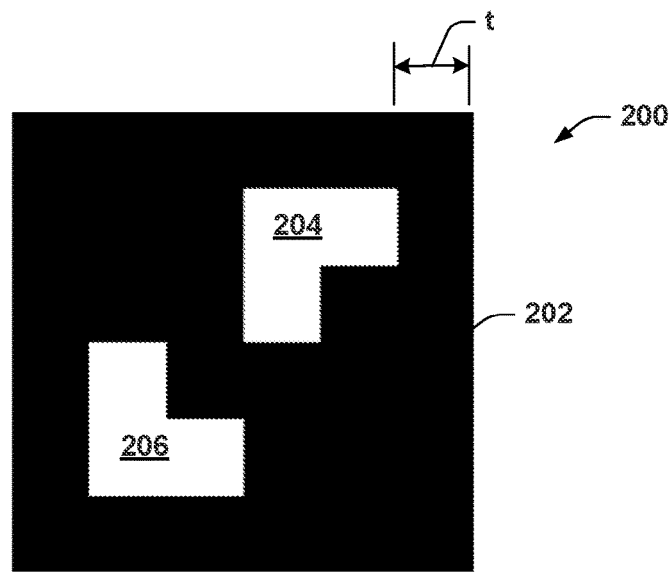
FIG. 3 depicts an example of a marker.

FIG. 3 depicts an example of a fiducial marker 200. As shown in this example, the marker includes black and white colors (e.g., binary) and includes a thick black rectangular (e.g., square) border 202 along each side of its entire peripheral edge (e.g., having a thickness t, such as one or more pixels thick). An interior of the marker 200 includes symbols 204 and 206 that can be used to define an orientation and/or other identifying feature for the marker, such as according to an AcUco library.

Figure 4A:
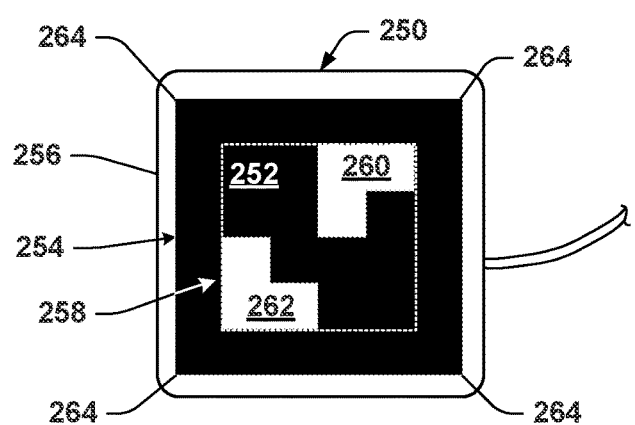
FIGS. 4A and 4B depict an example of a multi-modal marker.
Figure 4B:
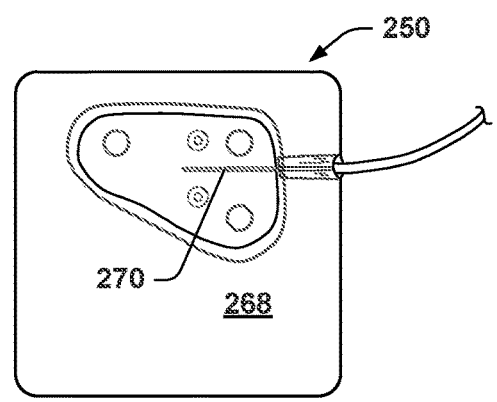

FIGS. 4A and 4B depict an example of a multi-modal marker device 250. The multi-modal marker can be fixed with respect to a patient (e.g., attached to the patient's body) during the acquisition of the first and second images using a 2D imaging modality, such as fluoroscopy or x-ray. FIG. 4A shows one side surface 252 of the marker device 250 that includes a fiducial marker (e.g., the marker of FIG. 3) 254 located within a white colored border 256 to provide contrast between the white border and a thick black border 258 of the fiducial marker (e.g., extending between dotted line and the white border 256). Symbols 260 and 262 are on the fiducial marker spaced apart from the black border 258.

As shown in FIG. 4B, as viewed from the other side showing surface 268 of the marker device 250, one or more tracking sensors (e.g., electromagnetic sensors) 270 are attached to the marker device 250 at known positions and orientations relative to the corners 264 of the fiducial marker 254. In one example, the one or more sensors 270 can respectively spatially sense a plurality of degrees of freedom (DOF). For example, the one or more sensors 270 can be configured to sense six (6) DOF, such as disclosed herein. In one example, the sensors 270 can be localized using an electromagnetic tracking system. The tracking system allows for determination of position and orientation of each sensor 270 based on a sensor signal provided from the sensor to the tracking system in response to an electromagnetic field. Other types of tracking systems configured to track the position and orientation of each sensor in three-dimensional space may be used in other examples.

In another example, the multi-modal marker may include a chamber between its side surfaces 252 and 268 that is configured to hold a volume of material (e.g., radiopaque material, such as a radiopaque contrast agent) to render a representation black portion of the marker visible in images acquired by the medical imaging modality. The chamber extends along and defines a rectangular-shaped thick border for the marker to define respective corners where edges thereof meet, which corners may be located in acquired images, as disclosed herein.

For example, the marker device 250 includes at least one port (e.g., in one of the surfaces 252, 268 or an edge of the device) to access the chamber such as to add and remove the radiopaque material with respect to the chamber. Each chamber thus can be filled with contrast to create an identifiable pattern in the two-dimensional projection images acquired by the medical imaging modality. Thus, when the material is in the chamber, the black portion of the fiducial marker is visible in medical images and when the radiopaque is removed, the black portion is visualized substantially the same as the white portion. For example, after the registration is complete (e.g., at least after the images have been acquired at 102 and 104 for registration), the contrast material would be drained out, and potentially flushed with clear saline solution, so that it does not interfere with subsequent imaging during the procedure. In other examples, the radiopaque material remains throughout the procedure.

Figure 5:
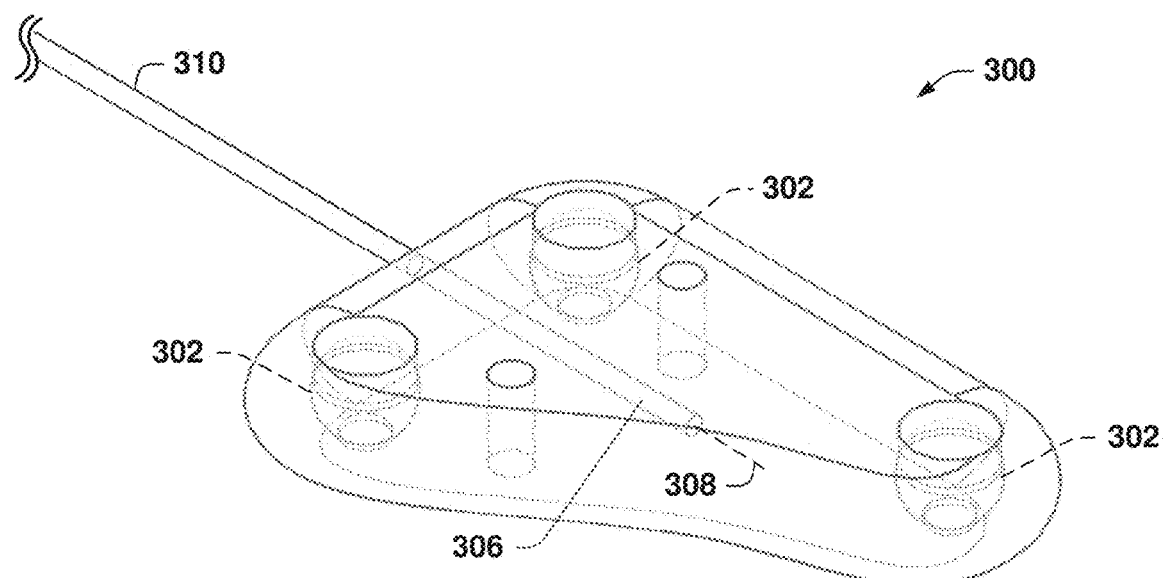
FIG. 5 depicts an example of another multi-modal marker.
Figure 6:
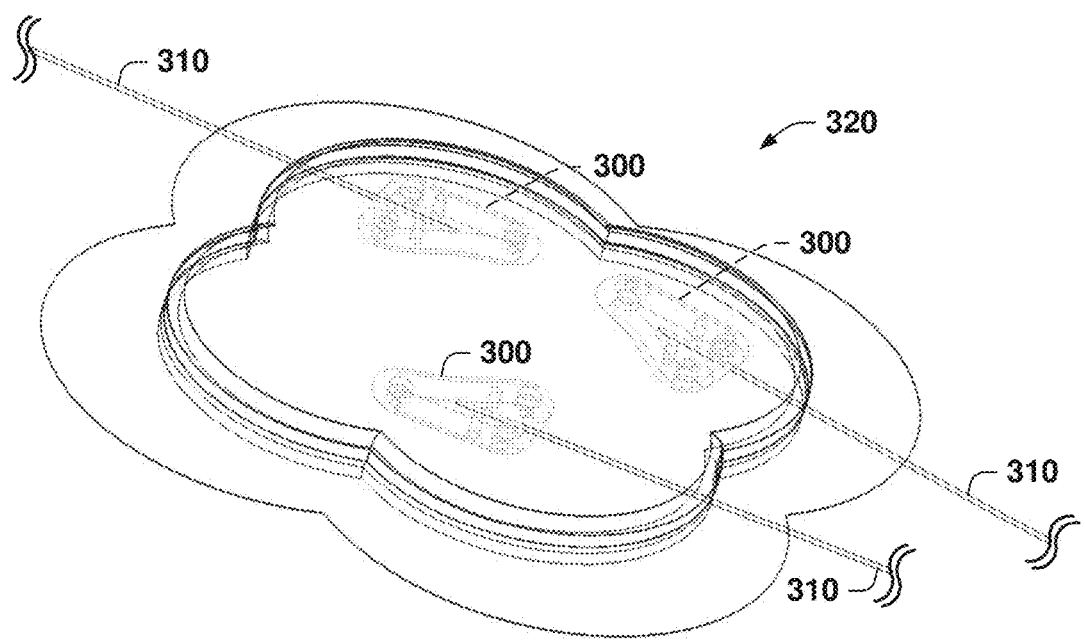
FIG. 6 demonstrates an example of marker pad device.

Other examples of a multi-modal marker device 300, which does not include the AruCo-type marker, are demonstrated in FIGS. 5 and 6. In the example of FIG. 5, the combination marker device 300 includes a plurality of radiopaque fiduciary objects 302 disposed within a substrate 304. Each of the radiopaque fiduciary objects 302 has a predetermined geometry and is arranged with a predetermined geometric relationship relative to each other. For example, the radio opaque objects 302 can be implemented as spheres or other shapes such as having a predetermined angular orientation and spatial arrangement (e.g., configured as a scalene right triangle). Thus, each of the radio opaque objects 302 can be identified in a corresponding 2D imaging modality (e.g., obtained intraprocedurally via a fluoroscopy, bi-plane x-ray or the like).

As mentioned, the type of material utilized for the respective objects 302 can vary depending upon the imaging modality being utilized (e.g., to acquire 2D images, such as at 102 and 104). The marker device 300 is a multimodal marker and, as such, also includes one or more sensors 306 detectable by the tracking system. Each sensor 306 can be dimensioned and located to have a predetermined spatial relationship (e.g., distance and angle) relative to the geometry of the respective radio opaque objects 302. For example, the sensor 306 can include a sensor coil that is positioned at the origin of a pair of axes that can be computed with respect to the geometric relationship of the objects 302. Additionally, the sensor itself 306 can extend along an axis 308 or be parallel to an axis defined by the respective radio opaque objects 302.

As a further example, the marker device 300 defines a coordinate system that includes X and Z axes lying in a virtual plane that extends through each of the objects 302 arranged in a triangle (of the page), with a corresponding Y axis extending perpendicular to the virtual plane (e.g., the page in which the figure is demonstrated). In an example, the central axis 308 of the sensor 306 extends along the Z axis of the coordinate system. A geometric center of a body of the sensor 306, thus may define the origin of the X, Y, and Z axes. As mentioned, the sensor 306 can be configured as an elongated coil that extends axially along a length of the Z axis, and is detectable by the tracking system. For example, the sensor 306 is implemented as a coil of electrically conductive material within the marker device 300 and a center of the sensor coil is located the origin of a corresponding coordinate system. The sensor 306 provides a sensor signal (e.g., an induced current signal) that is communicated to the tracking system in response to an electromagnetic field generated by a field generator of the tracking system.

FIG. 6 demonstrates an example of marker pad device 320 that can help protect the patient's skin from the hard surface of the combination markers. One or more of the multi-modal marker devices 300 (FIG. 5) can be implemented within the pad device 320 to enable co-registration between the domain of the tracking system and domain of the medical imaging modality, such as disclosed herein (e.g., fluoroscopy or the like). For example, the pad 320 can contain a gel or other soft flexible material to provide a cushion around each combination marker and the pad may be attached to the patient's skin. In other examples, the pad 320 is placed adjacent to the patient, such as on a bed next to or beneath the patient.

In the example of FIG. 6, the pad device 320 includes three of the multi-modal markers 300 distributed in a spaced apart arrangement with respect to each other. The pad device 320 can be configured to hold each of the combination markers in a substantially fixed spatial relationship while allowing flexibility to accommodate patient movement. Each of the marker devices 300 also includes a corresponding connection 310 that can be coupled to the tracking system. For example, the tracking system can be implemented as an electromagnetic tracking system, such as disclosed herein, and each of the connections 115 thus includes an electrical connector to provide an electrical signal to the tracking system, representing induced current in response to an electromagnetic field that is generated by a transmitter of the tracking system and detected by the respective sensing coil. In other examples, the connections can be wireless and the sensors can communicate via RF or other wireless technology. The tracking system can convert the sensor signals into corresponding tracking system data, which can be analyzed as disclosed herein. For example, the tracking data can include a position and orientation of a point in a three-dimensional coordinate space of the tracking system (also referred to herein as tracking system space) for each marker device 104.

FIGS. 7A and 7B depict a schematic example of a medical imaging modality 350 that can be used to acquire two-dimensional projection images from different viewing angles. For example, the medical imaging modality 350 is configured to acquire images using an ionizing radiation (e.g., a fluoroscopy system, a portable X-ray system or the like). In this example, the imaging modality 350 includes an X-ray source 352 configured to provide ionizing radiation (e.g., X-rays) and a detector 354 that are attached and held at a desired spaced apart position by a moveable C-arm 356. A patient can be position along with one or more marker devices 360 between the source 352 and detector 354. Thus, images acquired can vary depending on the viewing angle (e.g., axis) of the source and detector as adjusted by adjusting the position of the C-arm. For registration purposes, the viewing angle includes a region of interest of the patient and the marker 360.

By way of example, the registration is performed by modeling the X-ray source 352 as an ideal pinhole camera (i.e., assuming no distortion), where each pixel in the resulting image is formed by projecting 3D points into the image plane using a perspective transform such as follows:

$$s \begin{bmatrix} u \\ v \\ 1 \end{bmatrix} = \begin{bmatrix} f_x & 0 & c_x \\ 0 & f_y & c_y \\ 0 & 0 & 1 \end{bmatrix} \begin{bmatrix} r_{11} & r_{12} & r_{13} & t_1 \\ r_{21} & r_{22} & r_{23} & t_2 \\ r_{31} & r_{32} & r_{33} & t_3 \end{bmatrix} \begin{bmatrix} X \\ Y \\ Z \\ 1 \end{bmatrix}$$

where:
X, Y, and Z are the coordinates of a 3D point in the common coordinate system;
u and v are the coordinates of the projection point in the camera image in pixels;
fx and fy are the focal lengths in pixel units;
cx and cy is the image center in pixel units; and
r ## and t # define the position and orientation, respectively, of the X-ray detector in the common coordinate system.

To create the vector v1 or v2, the corners of the ArUco marker 360 are located in the image as u and v. The remaining values of the equation can be filled in based on the known spatial locations, and the equation is solved for X and Y at the focal length (e.g., distance between the detector and the respective corner location). The vector is then computed by subtracting the detector position (p1 or p2) from this new location. For example, points p1 and p2 are defined based on the rotation angle of the C-arm for the two projections, where the center of rotation is defined as the origin and the distance from the center is based on the C-arm radius. The focal length of the camera is computed from the pixel dimensions stored in the associated DICOM files.

The 3D position of the corner of the ArUco marker can then be computed by finding the intersection (or nearest approach) of the two vectors v1 and v2. The position and orientation of the ArUco marker in the common coordinate system is computed by repeating this process for all 4 corner locations identified for the fiducial marker in each of the respective images. By way of example, intersection (or nearest approach) of the two vectors may be computed according to a vector crossing function implementing a closest point function. As an example, the following pseudo-code implements a closest point function to determine a closest point between respective vectors:

```
vector ClosestPoint(vector p1, vector v1, vector p2, vector v2)
{
  // normalize direction vectors
  v1 = normalize(v1);
  v2 = normalize(v2);
  // check that the vectors are not co-incident (parallel)
  float projDir = dot_product(v1, v2);
  if (absolute_value(projDir) > 0.9999f)
  {
    // vectors are nearly co-incident (parallel)
    return p1;
  }
  // compute nearest point
  float proj1 = dot_product(p2 − p1, v1);
  float proj2 = dot_product(p2 − p1, v2);
  float dist1 = (proj1 − (projDir * proj2)) / (1 − (projDir * projDir));
  float dist2 = (proj2 − (projDir * proj1)) / ((projDir * projDir) − 1);
  vector pointOnLine1 = p1 + (dist1 * v1);
  vector pointOnLine2 = p2 + (dist2 * v2);
  return linear_interpolate(pointOnLine1, pointOnLine2, 0.5f);
}
```

In the example of FIGS. 7A and 7B, the marker 360 is demonstrated as an AruCo type radiopaque marker (e.g., corresponding to marker device 200, 250). In other examples, the medical imaging modality may be use with different types of marker devices, as disclosed herein, namely, the multi-modal marker device 300 and combination marker system 320. The respective transforms, such as determined at 108 and 154 (e.g., respective transformation matrices) thus can be used to enable rendering one or more visualizations based on the 2D image data acquired by the medical imaging modality 350, 3D preoperative image data and real-time tracking data.

Figure 8:
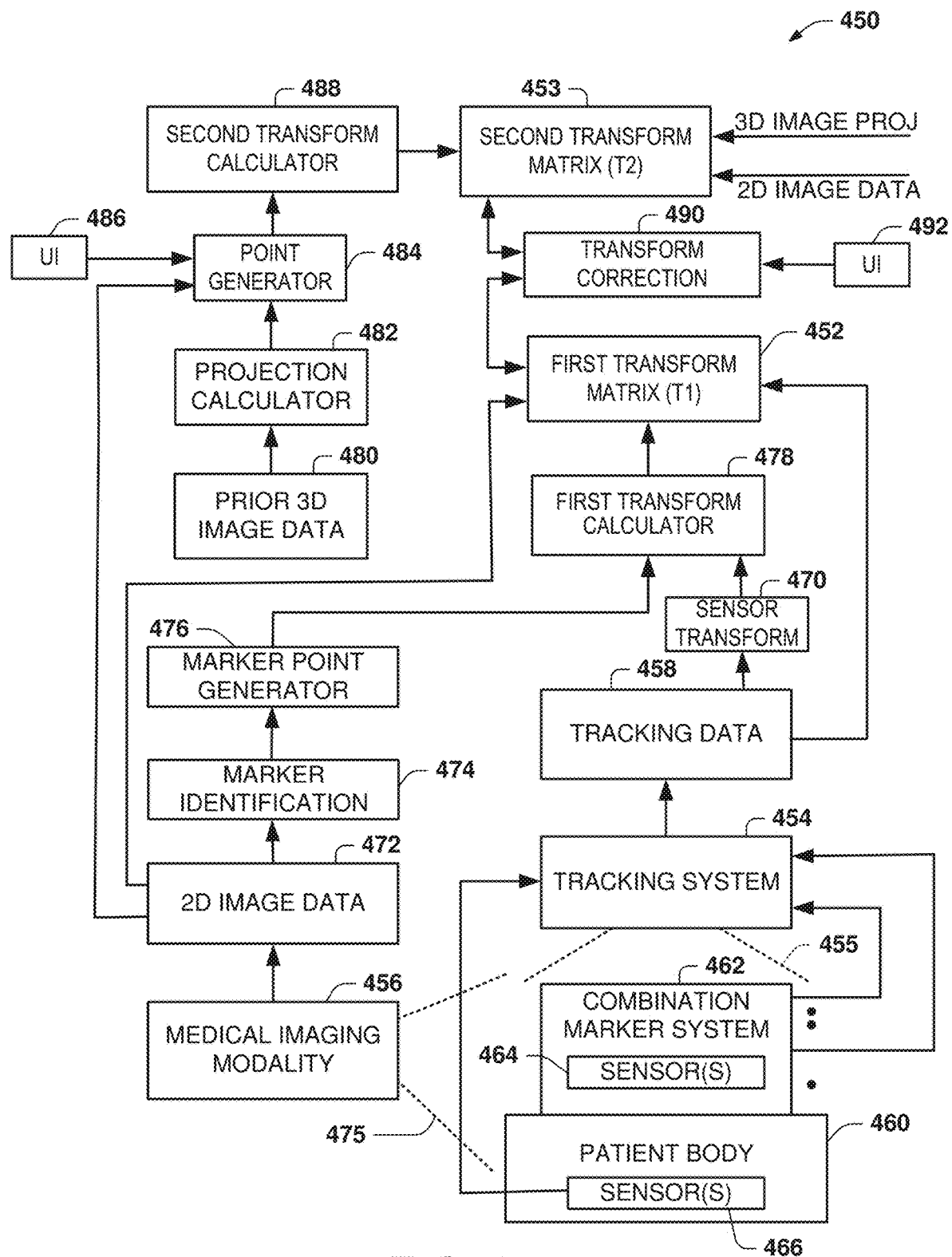
FIG. 8 depicts an example of a system for generating affine transformations.

FIG. 8 depicts an example of a system 450 for generating affine transformations. In this example, the affine transformations are demonstrated as transform matrices 452 and 453 for registering tracking data and image data, as disclosed herein. The system 450 is described in the context of data and instructions and a processor can access the data and execute the instructions to perform the functions disclosed herein. It is to be understood that not all functions may be required to implement the system. For example, each of the different transform matrices may be separately generated, which affords advantages when an imaging modality changes or is replaced in another implementation, the entire system does not need to be modified.

In the example of FIG. 8, the system 450 is configured for generating a first transform matrix (T1) 452. The transform matrix T1 may be configured to transform from a tracking system coordinate system of a tracking system 454 into a coordinate system of a medical imaging modality 456 (e.g., a 2D imaging system such as fluoroscopy or x-ray) and/or from the coordinate system of the medical imaging modality to the tracking coordinate system. The tracking system 454 is configured to provide tracking data 458 to represent a position and orientation of one or more sensors 466 being positioned within a patient's body 460.

A combination marker system 462 (e.g., including one or more multi-modal marker of FIG. 4A, 4B, 5 or 6) can be attached to the patient's body 460 or placed near the patient' body. In the example of FIG. 8, the combination marker system 462 can include one or more tracking sensors 464 that provide respective sensor signals to the tracking system 454 representative of a location of the combination marker within the coordinate system of the tracking system 454. In an example, the one or more object sensors 466 can be affixed relative to an object that is movable within the patient's body 460 for identifying a location of such sensor in the coordinate system of the tracking system. Each such object sensor 466 thus can also provide a signal to the tracking system 454 based on which the tracking system can compute corresponding tracking data representative of the position and orientation of such sensor in the tracking system coordinate system. As mentioned, the tracking data 458 thus represents a position and orientation of each respective object tracking sensor 466 as well as marker tracking sensors 464 of the multi-modal marker system 462.

In some examples, such as for purposes of generating the transform matrix 452, the sensor(s) 466 and corresponding tracking data 458 may be ignored (or omitted). In other examples, the sensor 466 may be placed at a known location with respect to the patient's body 460 (e.g., a known anatomical landmark within or external to the patient's body) to provide additional data points, in both the tracking system spatial domain (e.g., provided by tracking data 458) and the spatial domain of the imaging modality 456 (e.g., provided by 2D image data 472 at the known location) that may be used to facilitate generating the transform matrix T1 452.

By way of example, the tracking system 454 can include a transmitter (e.g., an electromagnetic field generator) that provides a non-ionizing field, demonstrated at 455, which is detected by each sensor 464 and 466 to provide a corresponding sensor signal to the tracking system. An example tracking system 454 is the AURORA spatial measurement system commercially available from Northern Digital, Inc., of Ontario, Canada. The tracking system 454 can provide the tracking data 458 at an output sample rate (e.g., sixty samples per second) for each sensor sufficient to enable substantially real time determination of sensor location (e.g., to provide a vector describing sensor position and orientation). A tracking processing subsystem thus can process each frame of tracking data such that the tracking data can likewise represent real time tracking data acquired by the tracking system that can be registered into another coordinate system by applying one or more of the generated transforms 452 and/or 453 to facilitate generating a graphical representation in a given domain, as disclosed herein.

The tracking system 454 may provide the tracking data 458 with an output sample rate to enable computation of real time positioning and visualization of the object to which the sensor is attached as well as the combination marker system. Since the marker system 462 is attached to the patient's body 460, the tracking system 454 computes the tracking data 458 to accommodate for movement in the patient's body 460 in the coordinate system of the tracking system 454.

A sensor transform 470 is configured to convert the tracking data 458 into locations for radiopaque objects implemented on each respective marker device, such as disclosed herein. Each of locations are 3D spatial coordinates in tracking system coordinate space and may remain fixed if the marker device does not move in the tracking space or may vary over time if the marker device moves in tracking space. For example, in the tracking coordinate system, each of the radiopaque markers of a given marker device are at fixed, known offsets (e.g., a 3D vector) from the location of the tracking sensor 464 that is part of the given marker device of marker system 462. As mentioned, the marker system may include a plurality of multi-modal marker devices, such as AruCo type (e.g., device 250), or other marker configurations (e.g., device 300) as disclosed herein.

The sensor transform 470 thus is configured to compute the points (e.g., 3D coordinates for marker locations) in the tracking system space based on the tracking data 458 and the known offsets for each tracking sensor relative to the pre-determined marker locations. For the AruCo type multi-modal marker device, the marker locations may be a set of four points (e.g., emPoint_1, emPoint_2, emPoint_3, emPoint_4) at the corners of the marker, such as disclosed herein. For example, the points in tracking system space for a set of marker locations of the AruCo type marker device having a sensor providing tracking data may be computed for a given marker device by multiplying the sensor transform (TS), which includes tracking sensor 3D coordinates, and the respective offset, as follows:

emPoint_1=mult($Ts$,offset_1), emPoint_2=mult($Ts$,offset_2), emPoint_3=mult($Ts$,offset_3), and emPoint_4=mult($Ts$,offset_4)

For the example of a marker device (e.g., for marker device 300) that includes an arrangement of spherical radiopaque markers, there are 3 spherical markers at known offsets distributed around each tracking sensor. Accordingly, the sensor transform will generate three points for each marker device in the marker system 462. For example, the transform 470 can determine marker locations at points (e.g., emPoint_1, emPoint_2, emPoint_3) located at the center of each of the spherical marker based on multiplying the respective transform and the known offset (e.g., 3D offset vector) between the tracking sensor location (e.g., a 3D point) and the respective radiopaque objects, such as follows:

emPoint_1=mult($Ts$,offset_1), emPoint_2=mult($Ts$,offset_2), and emPoint_3=mult($Ts$,offset_3).

Other deterministic locations having fixed offsets associated with the radiopaque markers may be used in other examples. In some examples the points may be arranged in a set of point for each marker device or as a single set that contains all the points.

The medical imaging modality 456 is configured to generate 2D image data 472 that includes at least two images (e.g., radiographs) representing objects within a field of view 475 of the imaging modality 456. For example, the imaging modality may include a fluoroscopy scanner (e.g., the system of FIGS. 7A and 7B) configured to acquire the 2D image data for a small number of (e.g., at least two, three or four) 2D projection images acquired at different viewing angles relative to the patient's body 460. Each of the images in the image data 472 may be acquired to include a 2D projection for radiopaque markers in each marker device of the marker system 462 and a region of the patient's body 460 within the field of view 475. In some examples, the region of the patient's body may be a region of interest in which the object sensor 466 is to be moved, such as part of a surgical procedure.

A marker identification function 474 can be configured to locate each radiopaque marker (e.g., AruCo marker and/or other object marker) in each image provided in the image data 472. The radiopaque markers will be visible in the images due to their opacity with respect to the ionizing radiation emitted by the imaging modality 456. For the example of the combination marker that includes an AruCo-type marker, an AruCo detection function may be invoked by marker identification function 474 to locate each respective marker. For an example combination marker that includes a radiopaque object other than an AruCo type marker, a periphery of each such marker may thus be localized by image thresholding as well as other image processing techniques applied to values of image pixels. The marker identification function 474 may be fully automated and/or be user-interactive in response to a user input identifying the markers. The identified markers (e.g., pixel locations in the respective images) may be stored in memory for further processing.

A marker point generator 476 is programmed to generate spatial coordinates for each marker identified in the (e.g., two or more) images provided by the image data 472. For the example of the combination marker that includes a radiopaque AruCo type marker, the spatial coordinates may be generated for each of the corners of each marker, namely, coordinates for a set of four points surrounding each tracking sensor. For spherically shaped radiopaque markers, the spatial coordinates for each marker are provided as 2D coordinates at a center of the circular projection (e.g., the periphery identified by marker identification function 474) in each 2D image for the viewing angle provided by the field of view 475 relative to the marker system 462. In an example where three spherical markers surround each tracking sensor for a given marker device, the marker point generator is programmed to provide coordinates for a set of three points for the given marker device. Regardless of the type and configuration of radiopaque marker, the marker point generator for example, is programmed to execute a closest point function such as disclosed herein, to locate the set of points around each respective tracking sensor for the marker device. In this way, each set of points can be linked together and associated with a respective one of the tracking sensors to facilitate generating the first transform matrix 452.

A first transform calculator 478 is programmed to compute the first transform matrix 452 based on the points provided by the marker point generator 476 and the sensor transform function 470. For example, the transform calculator 478 is applied to align the sets of points that have been measured in the spatial coordinate systems. Examples of such co-registration algorithm to co-register the points in the respective domains (e.g., tracking system coordinate system and medical imaging coordinate system) may include an error minimization function or a change of basis function.

As one example, the transform calculator 478 is programmed to implement an error minimization function. Given the ordered set of points, the transform calculator 478 is to determine unknown transform T1 that minimizes the distance between the projected location and the measured location. For example, for T1 the calculator 478 is programmed to find the transform that minimizes the distance between points, such as follows:

sum($n=1 \ldots i$,distance(mult($T1$,imPoint_$n$),em-Point_$n$)^2)

where: n denotes a given one of i points (i is the number of points for a given multi-modal marker;
imPoint_n is the spatial coordinates in image space for point n; and emPoint_n is the spatial coordinates in tracking space for point n.

In an example, the error minimization can be solved through Single Value Decomposition or any number of error minimization algorithms.

As another example, the transform calculator 478 is programmed to implement a change of basis function. If the points used are arranged in a way that allows transform calculator 478 to generate a set of basis vectors (x, y, and z unit vectors that define the coordinate space) then a simpler solution is possible compared to error minimization. For example, rather than minimizing the errors, the transform calculator 478 is programmed to find the basis vectors in both coordinate systems and apply them at a common point. This is computationally more efficient than the error minimization approached mentioned above, but requires a specific arrangement of points.

By way of example, to unambiguously define the basis vectors, the arrangement of points needed is 3 points at a 90 degree angle, with enough additional information to allow transform calculator 478 to identify which point is which (for example, having the legs of the triangle created by the 3 points be different lengths). Both the ArUco-type marker of FIGS. 3 and 4 and the marker devices of FIGS. 5 and 6, have arrangements of points sufficient enable the use of such change of basis function, with the caveat being that for the marker device of FIGS. 5 and 6, each set of 3 points needs to be treated separately.

In each coordinate system, the transform calculator 478 constructs the basis vectors from 3 points. For example, given point_1, point_2, and point_3 (e.g., vertices of a right triangle), provides two segments, one from point_2 to point_1 and another from point_2 to point_3, which segments are the legs of a right triangle. These points and segments provide the following basis vectors:

basis_z=normalize(point_1−point_2)

basis_x=normalize(point_3−point_2)

basis_y=cross(basis_x,basis_z)

From the basis vectors, the transform calculator 478 is programmed to create a matrix (e.g., a 4×4 matrix) that defines the position and orientation of point_2 as follows:

matrix=[basis_x.x,basis_y.x,basis_z.x,point_2.x,
  basis_x.y,basis_y.y,basis_z.y,point_2.y, basis_x.z,
  basis_y.z,basis_z.z,point_2.z, 0,0,0,1]

With that matrix defined in each coordinate system, the transform calculator 478 can compute the transform 452 between the two coordinate systems. For example, for the transform matrix T1:

im_Matrix is the matrix defined from the basis vectors in the medical imaging (e.g., intraoperative) coordinate system; and em_Matrix is the matrix defined from the basis vectors in the tracking coordinate system.

From the above, the transform calculator 478 may determine the transform matrix (T1) 452 by multiplying the basis vector tracking matrix (em_Matrix) and the inverse of the basis vector imaging matrix (inv(im_Matrix)), such as follows:

T1=mult(em_Matrix,inv(im_Matrix))

The transform matrix may be stored in memory and used for transforming from the tracking system space to the medical imaging space. For example, the position of the object sensor 466 within the patient's body, as represented by tracking data 458, may be registered into the medical imaging space by applying the transform T1 to the position and orientation information of the tracking data.

As mentioned, the system 450 also is configured to generate the second transform (T2) 453 for use in transforming between the medical imaging coordinate system and a coordinate system of prior 3D image data 480. For example, the prior 3D image data 480 may be stored in memory (e.g., as a DICOM image set) and include a 3D image from a preoperative scan (e.g., CT scan) of the patient's body 460 that is performed at a time prior to when the medical imaging modality 456 generates its image data 472 (e.g., intraoperatively, such as corresponding to images acquired at 102 and 104).

A projection calculator 482 (e.g., corresponding to the function 152 of FIG. 2) is programmed to generate a respective projection from the 3D image data 480 for each of the images (e.g., two images) provided in the 2D image data 472. The projection calculator 482 implements a function to map the points from the 3D image space onto a two-dimensional plane. For example, the projection calculator derives forward projections that are aligned with the viewing angles of the images in the 2D image data 472. The registration of projection angles for each of the 3D projections may be implemented through manual alignment and/or be automated. In an example, the alignment may be automated, such as based on image metadata (demonstrated as included in the arrow from the 2D image data 472 to projection calculator 482) in the image data 472 that describes the angle of each of the 2D images. For example, the metadata includes data specifying the projection angle, such as AP, LAO, RAO, such has may be known from the angle of a C-arm and/or be provided in response to a user input when the imaging modality 456 acquires the image data 472.

In some examples, as disclosed herein the 3D image data may include a model of one or more anatomical structure, such as in the form of a 3D mesh corresponding to a surface of a vessel. A 3D projection matrix (e.g., perspective or parallel projection matrix) may be applied to the mesh that was generated from the pre-operative image 480, such as disclosed herein. If the angle of the C-arm is known for each of the intraoperative images, one 3D projection of the mesh is performed to match the angle for each intraoperative image. If the angle of the C-arm is not known, multiple 3D projections may be generated along different angles, and there may be a manual or automated selection of a "best fit" match between the respective 3D projections and the respective two-dimensional image.

A point generator 484 is programmed to generate spatial points in each of the 2D images (provided by image data 472) and the corresponding projections of the 3D image (provided by projection calculator 482). Rather than working with spheres or corners of markers, the points are selected as features that are visible in both the 2D image data 472 and the 3D image data 480. For example, the features include structures such as bony landmarks on the spine, bits of calcification that are visible in both types of images, or points on vessels in an example when contrast is used in both images. Other feature or fiducial points may be used in other examples. In some examples, a common set of features may be located in an automated method (e.g., feature extraction). Additionally or alternatively, one or more such features may be selected in response to a user input provided through a user interface 486, such as graphical user interface interacting with the respective images and projections provided to the point generator. For instance, a user may see a common visible structure among the different views and select/tag it (e.g., through a mouse, keyboard, gesture or other input) in each view. The point generator 484 thus generates points for each predetermined feature and/or user selected feature. The point generator thus operates similarly to the marker point generator 476, just using a different set of landmarks. Since the image data 480 are in 3D, in some examples, the user can identify selected points (through user interface 486) using a set of orthogonal views (e.g., axial, coronal, and sagittal views) of the 3D images of image data 480 to directly measure the x, y, and z locations in the 3D coordinate system of the image data 480. Each of these locations may be converted to two-dimensional coordinates and provided as such in the forward projections provided by the projection calculator 482. The point generator 484 is programmed to locate the same points in the 2D image data, such as by using a vector-crossing function applied to the 2D images, such as the closest point function disclosed herein.

The resulting points in the respective images are provided to a second transform calculator 488 for generating the transform matrix 453. The transform calculator 488 is programmed to compute the transform matrix that aligns the images of the second image data with the 3D image data 480 based on the common points provided by the point generator 484. For example, the transform calculator 488 constructs the transform matrix (T2) 453 by implementing an error minimization function with respect to the common set of points, such as single value decomposition described with respect to the first transform calculator 478. Other error minimization functions may be used in other examples.

In some examples, the system 450 includes a transform correction function 490 programmed to implement manual corrections to one or both of the transform matrices 452 and 453 based on instructions provided via a correction user interface 492. Manual corrections can be applied even if with an estimate of the T1 or T2 transform is initially provided. For example, if the image data 480 and/or 472 does not have a well-defined set of measured points (e.g., on the spine or other anatomic structure) to work from to perform the registration, the system may define an initial estimate for the transform T2 or, in some examples, an arbitrary T2 transform (e.g. an 'identity' matrix) and allow the user to make corrections through the correction function 490 to generate the final T2 transform 453.

Figure 9:
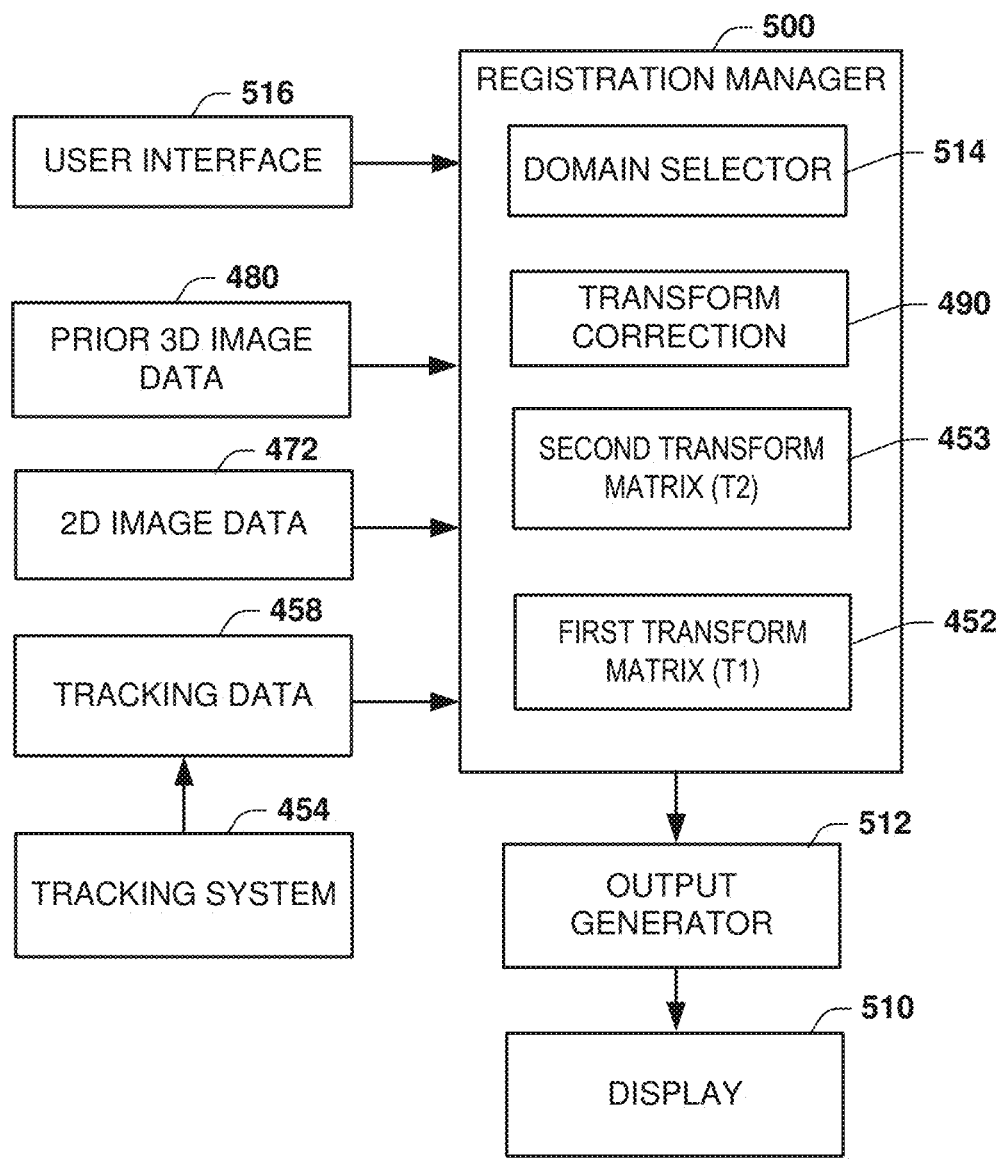
FIG. 9 depicts an example of a registration manager to control use or corrections to one or more affine transformations.

By way of further example, with reference to FIG. 9, a registration manager 500 is used to control user corrections to one or both transforms T1 and T2, 452 and 453, respectively. The registration manager may be implemented as part of the system 450 of FIG. 8 or as a separate function. Accordingly, for consistency, functions and data introduced in FIG. 8 are depicted in FIG. 9 using the same reference numbers. Reference may be made back to FIG. 8 and the corresponding description for further information about such functions and data.

The registration manager 500 includes the transform correction function 490 as well as the first and second transform matrices 452 and 453, respectively. In this example, it is assumed that one or both of the transform matrices 452 and 453 may be in need of correction. The need for correction may be made manifest to a user by applying a transform to register two or more domains and provide a resulting visualization on a display 510. For example, an output generator 512 is configured to render a visualization in a selected domain, such as may be the coordinate system of the tracking system, the coordinate system of the medical imaging modality 456 or the coordinate system of the prior 3D image data 480. In an example, the manager 500 includes a domain selector 514 programmed to select which domain the output visualization is being rendered based on a user input instruction received via a user interface 520. Additionally, based on the selected domain, the registration manager applies one or both of the transforms T1 or T2 accordingly. As an example, the following table provides a description of which one or more transforms are applied to the image data 472, 480 or tracking data 458 for each selected domain to which the output visualization is being rendered by the output generator 512. The registration manager 500 further may be used to control the application of the respective transforms to provide a visualization in a selected domain, such as by applying one or more transforms or inverses of such transforms as set forth in the table.

|  | Tracking | Medical Imaging | Prior 3D |
| --- | --- | --- | --- |
| to Tracking: | [identity] | inv(T1) | inv(T1) inv(T2) |
| to Medical Imaging: | T1 | [identity] | inv(T2) |
| to Prior 3D: | T2 T1 | T2 | [identity] |

As a further example, manual corrections to either transform 452 or 453 can be provided by multiplying the respective transform matrix T1 or T2 by a correction matrix, such as follows:

correctedT1=mult(correctionMatrix,*T*1) or correctedT2=mult(correctionMatrix,*T*2)

In an example, the supported types of corrections include translation, rotation and scaling, such as may be applied in the form of matrices, as follows:

translation Matrix=[1,0,0,translation.*x*, 0,1,0,translation.*y*, 0,0,1,translation.*z*, 0,0,0,1]

scaling Matrix=[scale,0,0,0,0, scale,0,0,0,0, scale,0,0, 0,0,1]

rotationMatrix=(depends on axis of rotation)

By way of further example, a user initiates corrections using mouse-down/drag/mouse-up actions or other actions on the user interface 516. The values used in the correction matrix may be set based on the projection matrix used to display the viewport on the display 510. For example, a translation initiated from an AP view would result in the X and Y mouse movements being used to set translation.x and translation.z values (translation.y would be 0). Such transformations thus allow the user to change the view of a single image or the alignment of multiple images.

As a further example, such as when implementing corrections for transform T2, the domain registration manager 500 applies the transform T2 to the image data 472 and the output generator 512 provides a visualization of the 2D images registered in the 3D image based on the transform T2. If the landmarks are properly aligned, as shown on the display 510, no correction may be needed. However, if the locations of landmarks in the 2D image do not align with their respective locations in the 3D image, correction may be needed to T2. A user thus can adjust the alignment of the 2D image with respect to the 3D image (or the forward projection thereof) through the user interface 516. As mentioned, the adjustments may include translation in two dimensions, rotation and/or scaling in response to instructions entered through the user interface using an input device (e.g., mouse or keyboard). The output generator 512 may update the visualization shown in the display to show the image registration in response each adjustment (e.g., in real time). Once a desired alignment is visualized, the user can employ the user interface 516 to apply and store the corrections to the transform T2, and an updated T2 may be stored in memory for subsequent applications. Similar types of adjustments may be made with respect to the first transform matrix 452.

Figure 10A:
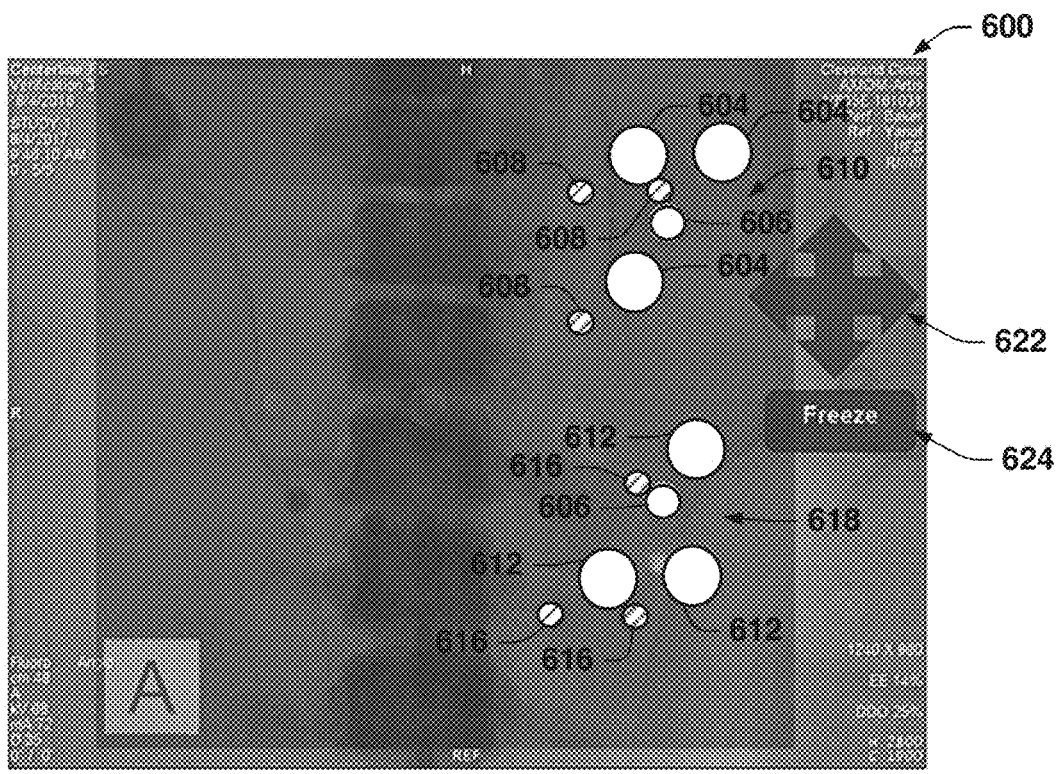
FIGS. 10A and 10B depict graphical representations of information registered in a given domain according to an affine transformation.
Figure 10B:
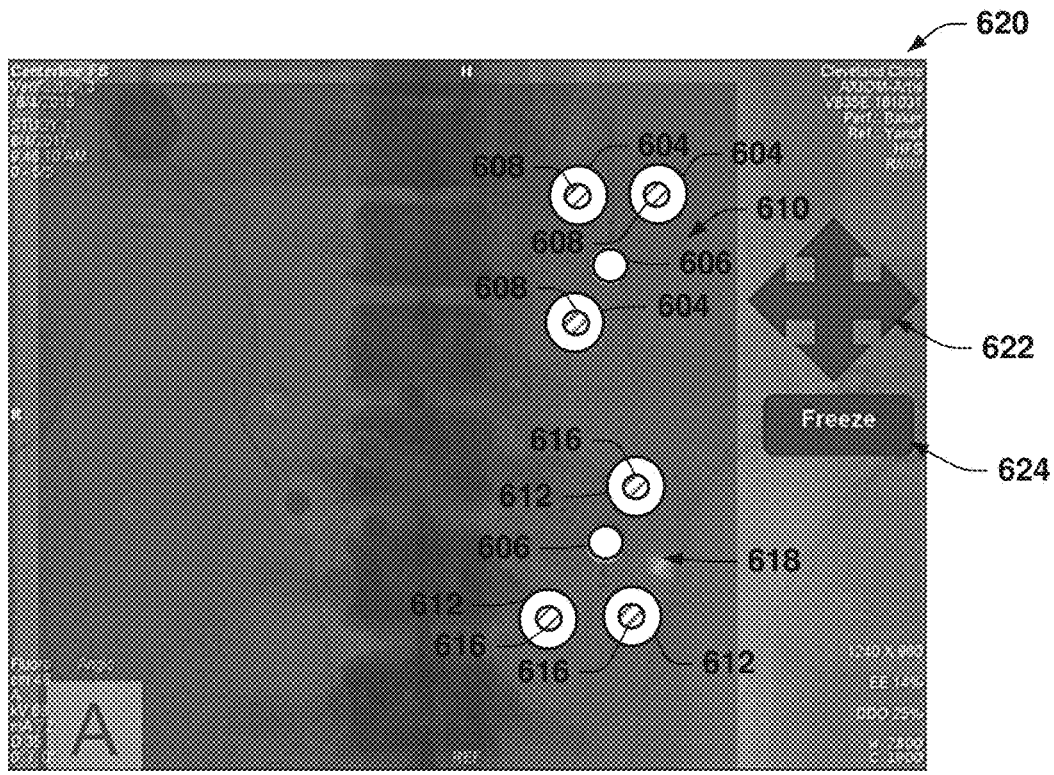

FIGS. 10A-10B demonstrate examples of images 600 and 630 that may be generated and visualized in a display (display 510) according to application of one or more transforms before and after manual correction (e.g., implemented by correction function 490). In both FIGS. 10A and 10B the images include a common set of anatomical features and marker features. For example, the anatomical feature includes vertebrae of a spine 602. The marker features for a given marker device 610 include locations of radiopaque markers 604 and a tracking sensor 606 that have been mapped by applying a transform from one image space (e.g., the tracking system coordinate system) to another (e.g., the medical imaging coordinate system). The marker features for the marker device 610 also include locations of radiopaque markers 608 in their original domain (e.g., the medical imaging coordinate system). The images also include marker feature for another marker device 618, including locations of radiopaque markers 612 and a tracking sensor 614 that have been mapped by applying a transform from one image space (e.g., the tracking system coordinate system) to another (e.g., the medical imaging coordinate system) as well as locations of radiopaque markers 616 in their original domain (e.g., the medical imaging coordinate system).

As shown in FIG. 10A, the respective marker features and anatomical feature are not aligned due to misregistration. As disclosed herein, the output display is interactive and includes a GUI element 622 that may be used to adjust (e.g., translate, rotate or scale) one of the images relative to the other. In response to such adjustments the correction function 490 generates one or more correction matrices, such as disclosed herein. Once a desired alignment is achieved, such as shown in the visualization 630 of FIG. 10B, the user can activate a "Freeze" GUI element (a button) 624 to apply the corrections to the appropriate transform(s), and the updated transform can be stored in memory for further applications.

In some examples, after the first step is performed with an AP image, the system should have registration in two dimensions—patient left-to-right and head-to-foot. The procedure above may be repeated with a lateral or oblique view to get the third dimension—patient anterior to posterior. In a further example, if a user were to advance a catheter or guidewire (e.g., including a tracking sensor) near the aortic bifurcation or other identifiable landmark, a rough registration in that third dimension could be performed without a second 2D medical image.

By way of example, the two-dimensional image data may include one two-dimensional image acquired by the medical imaging modality (e.g., intraoperatively) to include the patient and the multi-modal marker, such that predetermined portions of the multi-modal marker being visible in the 2D image and have a known location and orientation with respect to at least one tracking sensor detectable by a tracking system. A three-dimensional position for predetermined portions of the multi-modal marker may be estimated with respect to a coordinate system of the medical imaging modality according to respective locations of the predetermined portions of the mark in each one (or more) of the two-dimensional images. An affine transformation is determined for registering the three-dimensional coordinate system of the tracking system with the three-dimensional coordinate system of the medical imaging modality based on the estimated position for the respective predetermined portions of the multi-modal marker and the known (a priori) relationship of the at least one tracking sensor (e.g., including the tracking sensor on the guidewire or catheter at the known landmark) and the predetermined portions of the multi-modal marker. Thus, a second 2D image may be omitted and still enable registration.

In view of the foregoing structural and functional description, those skilled in the art will appreciate that portions of the systems and method disclosed herein may be embodied as a method, data processing system, or computer program product such as a non-transitory computer readable medium. Accordingly, these portions of the approach disclosed herein may take the form of an entirely hardware embodiment, an entirely software embodiment (e.g., in one or more non-transitory machine-readable media), or an embodiment combining software and hardware. Furthermore, portions of the systems and method disclosed herein may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general-purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions that implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of components or methodologies, but one of ordinary skill in the art will recognize that many further combinations and permutations are possible. Accordingly, the invention is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A method comprising:
acquiring a first two-dimensional projection image using a medical imaging modality, the first projection image including a two-dimensional field of view that includes a patient and a multi-modal marker;
acquiring a second two-dimensional projection image using the medical imaging modality, the second projection image including the patient and the multi-modal marker and being along a non-coincident angle with respect to the first projection image, predetermined portions of the multi-modal marker being visible in the first projection image and the second projection image and having a known location and orientation with respect to at least one sensor that is detectable by a tracking system, wherein the at least one sensor is attached to the multi-modal marker or the multi-modal marker includes the at least one sensor;
estimating a three-dimensional position for the predetermined portions of the multi-modal marker with respect to a coordinate system of the medical imaging modality according to locations of the predetermined portions in each of the respective first and second projection images; and
determining an affine transformation for registering a three-dimensional coordinate system of the tracking system with a three-dimensional coordinate system of the medical imaging modality based on the estimated position for the respective predetermined portions of the multi-modal marker and a known relationship of the at least one sensor and the predetermined portions of the multi-modal marker.

2. The method of claim 1, wherein the affine transformation is a first affine transformation, the method further comprising:
deriving respective forward projections from a prior three-dimensional image that correspond to each of the first two-dimensional projection image and the second two-dimensional projection image; and
determining a second affine transformation from the coordinate system of the medical imaging modality to the coordinate system of the prior three-dimensional image based on registering the first and second projection images with the respective forward projections.

3. The method of claim 2, wherein a three-dimensional mesh model is derived from the prior three-dimensional image to represent an anatomical structure of the patient in the coordinate system of the prior three-dimensional image, and
wherein the respective forward projections from the prior three-dimensional image are determined based on the mesh model.

4. The method of claim 2, wherein determining the second affine transformation further comprises:
identifying a common set of features in each of the first and second projection images and the prior three-dimensional image;
determining locations for at least some of the common set of features in the coordinate system of the medical imaging modality and in the coordinate system of the prior three-dimensional image; and
computing the second affine transformation as a respective transform matrix configured to align the locations determined for the common set of features in one of the coordinate system of the medical imaging modality or the coordinate system of the prior three-dimensional image.

5. The method of claim 2, wherein the first affine transformation is computed by one of an error minimization function or a change of basis function, and
wherein the second affine transformation is computed by an error minimization function.

6. The method of claim 1, wherein the multi-modal marker includes a chamber and at least one port to access the chamber, the chamber having a predetermined spatial position and orientation with respect to each sensor,
wherein the multi-modal marker is fixed with respect to the patient during the acquisition of the first and second projection images, and
wherein the multi-modal marker includes a contrast agent within the chamber during the acquisition of the first and second projection images such that the chamber is visible in each of the first and second projection images, the method further comprising:
adding a volume of the contrast agent to the chamber via the port before the acquisition of the first and second projection images to render the chamber visible in images acquired by the medical imaging modality; and
removing the contrast agent from the chamber after the acquisition of the first and second projection images such that the chamber is not visible in subsequent images acquired by the medical imaging modality.

7. The method of claim 1, wherein the medical imaging modality is configured to acquire images using an ionizing radiation.

8. The method of claim 7, wherein the medical imaging modality comprises a C-arm having a center of rotation, the method further comprising defining an origin of the coordinate system of the medical imaging modality with respect to the center of rotation of the C-arm.

9. The method of claim 1, wherein the first and second projection images are selected from a group comprising: a right anterior oblique projection, a left anterior oblique projection and an anterior-posterior projection.

10. The method of claim 1, wherein the non-coincident angle is less than or equal to 90 degrees.

11. A system comprising:
one or more non-transitory computer-readable media to store data and instructions executable by a processor, the data comprising:
two-dimensional image data that includes at least one two-dimensional image acquired by a medical imaging modality to include a patient and a multi-modal marker, predetermined portions of the multi-modal marker being visible in the at least one two-dimensional image and having a known location and orientation with respect to at least one tracking sensor that is detectable by a tracking system, wherein the at least one tracking sensor is attached to the multi-modal marker or the multi-modal marker includes the at least one tracking sensor;
the instructions programmed to perform a method comprising:
estimating a three-dimensional position for predetermined portions of the multi-modal marker with respect to a coordinate system of the medical imaging modality according to respective locations of the predetermined portions in each of the at least one two-dimensional image; and determining an affine transformation for registering a three-dimensional coordinate system of the tracking system with a three-dimensional coordinate system of the medical imaging modality based on the estimated position for the respective predetermined portions of the multi-modal marker and a known relationship of the at least one tracking sensor and the predetermined portions of the multi-modal marker.

12. The system of claim 11, wherein the at least one two-dimensional image is a first two-dimensional image, and wherein the two-dimensional image data further includes a second two-dimensional image acquired by the medical imaging modality, the second two-dimensional image including the patient and the multi-modal marker and being along a non-coincident angle with respect to the first two-dimensional image.

13. The system of claim 11, wherein the affine transformation is a first affine transformation and the method performed by the instructions further comprises:

deriving respective forward projections from a prior three-dimensional image that correspond to each two-dimensional image; and determining a second affine transformation between the coordinate system of the medical imaging modality and the coordinate system of the prior three-dimensional image based on registering each of the two-dimensional images with the respective forward projections.

14. The system of claim 13, wherein a three-dimensional mesh model is derived from the prior three-dimensional image to represent an anatomical structure of the patient in the coordinate system of the prior three-dimensional image, and wherein the respective forward projections from the prior three-dimensional image are determined as projections based on the mesh model.

15. The system of claim 13, wherein determining the second affine transformation further comprises:

identifying a common set of features in the prior three-dimensional image and each of the two-dimensional images and;

determining locations for at least some of the common set of features in the coordinate system of the medical imaging modality and in the coordinate system of the prior three-dimensional image; and computing the second affine transformation as a respective transform matrix configured to align the locations determined for the common set of features in one of the coordinate system of the medical imaging modality or the coordinate system of the prior three-dimensional image.

16. The system of claim 13, wherein the first affine transformation is computed by one of an error minimization function or a change of basis function, and wherein the second affine transformation is computed by an error minimization function.

17. The system of claim 11, further comprising the multi-modal marker, the multi-modal marker including a chamber and at least one port to access the chamber, the chamber having a predetermined spatial position and orientation with respect to the at least one tracking sensor, wherein the multi-modal marker is fixed with respect to the patient during the acquisition of the first and second images, and wherein the multi-modal marker includes a volume of fluid contrast agent within the chamber during the acquisition of the first and second images such that the chamber is visible in each of the first and second images.

18. The system of claim 11, further comprising the medical imaging modality, wherein the medical imaging modality is configured to acquire each of the at least one two-dimensional image using an ionizing radiation.

19. The system of claim 18, wherein the medical imaging modality comprises a C-arm having a center of rotation, wherein an origin of the coordinate system of the medical imaging modality is defined with respect to the center of rotation of the C-arm.

20. The system of of claim 12, wherein the non-coincident angle is less than or equal to 90 degrees.

21. A system comprising:

one or more non-transitory computer-readable media to store data and instructions executable by a processor, the data comprising:

prior three-dimensional image data acquired for a patient;

two-dimensional image data that includes at least one two-dimensional image acquired by a medical imaging modality to include the patient and a multi-modal marker, predetermined portions of the multi-modal marker being visible in the at least one two-dimensional image and having a known location and orientation with respect to at least one tracking sensor that is detectable by a tracking system, wherein the at least one tracking sensor is attached to the multi-modal marker or the multi-modal marker includes the at least one tracking sensor;

the instructions programmed to perform a method comprising:

deriving respective forward projections from the prior three-dimensional image data that correspond to each two-dimensional image; and determining an affine transformation between a coordinate system of the medical imaging modality and a coordinate system of the prior three-dimensional image based on registering each two-dimensional image with the respective forward projections.

22. The system of claim 21, wherein the affine transformation is a first affine transformation, and the method performed by the instructions further comprises:

estimating a three-dimensional position for predetermined portions of the multi-modal marker with respect to the coordinate system of the medical imaging modality according to respective locations of the predetermined portions in each of the at least one two-dimensional image; and determining a second affine transformation for registering a three-dimensional coordinate system of the tracking system with a three-dimensional coordinate system of the medical imaging modality based on the estimated position for the respective predetermined portions of the multi-modal marker and a known relationship of the at least one tracking sensor and the predetermined portions of the multi-modal marker.

23. The system of claim 21, wherein the at least one two-dimensional image is a first two-dimensional image, and wherein the two-dimensional image data further includes a second two-dimensional image acquired by the medical imaging modality, the second two-dimensional image including the patient and the multi-modal marker and being along a non-coincident angle with respect to the first two-dimensional image.

\* \* \* \* \*